United States Patent [19]

Mixich et al.

[11] 4,124,767

[45] Nov. 7, 1978

[54] IMIDAZOLYL-OXIME ETHERS HAVING ANTI-MYCOTIC AND BACTERICIDAL ACTIVITY

[75] Inventors: Georg Mixich; Kurt Thiele, both of Zofingen; Johanna Fischer, Reiden, all of Switzerland

[73] Assignee: Siegfried A.G., Zofingen, Switzerland

[21] Appl. No.: 754,691

[22] Filed: Dec. 27, 1976

[30] Foreign Application Priority Data

Dec. 24, 1975 [CH] Switzerland ............... 16768/75

[51] Int. Cl.$^2$ ............................................ C07D 233/60
[52] U.S. Cl. ................................. 548/341; 424/273 R
[58] Field of Search ..................... 260/309; 424/273; 548/341

[56] References Cited

U.S. PATENT DOCUMENTS

| 3,515,728 | 6/1970 | Henry et al. ............... 260/309 |
| 3,818,029 | 6/1974 | Regel et al. ............... 548/336 |
| 3,951,963 | 4/1976 | Winkelmann et al. ............... 260/309 |

OTHER PUBLICATIONS

Godefroi et al., J. Med. Chem., 1969, vol. 12, pp. 784-791.

*Primary Examiner*—Natalie Trousof
*Attorney, Agent, or Firm*—Finnegan, Henderson, Farabow & Garrett

[57] ABSTRACT

Imidazolyl oxime ethers (I) are disclosed which contain an aromatic or heteroaromatic grouping linked to the carbon atom of the oxime ether, the oxime being etherified by a variety of groups; aliphatic, aromatic, heteroaromatic, cycloaliphatic and aliphatic substituted by aromatic, heteroaromatic or cycloaliphatic groups. The compounds are obtained from the corresponding ketones by reaction with O-substituted hydroxylamines or by reaction of metal oximates with halides of the required etherifying group. The said products (I) possess antimycotic and bactericidal activity.

14 Claims, No Drawings

IMIDAZOLYL-OXIME ETHERS HAVING ANTI-MYCOTIC AND BACTERICIDAL ACTIVITY

This invention relates to new imidazoyloxime ethers. According to the present invention, there are provided imidazolyl oxime ethers of the general formula:

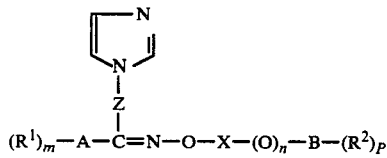

in the form of either of its two possible geometric isomers or a mixture thereof in free base form or therapeutically effective salt form as a result of reaction with an acid, in which formula:

Z is selected from the group consisting of straight and branched chain $C_1$-$C_4$ alkylene groups, A is selected from the group consisting of phenyl and naphthyl, $R_1$ is selected from the group consisting of halogen, nitro, $C_1$-$C_6$ alkyl and $C_1$-$C_6$ alkoxy, X is a $C_1$-$C_8$ alkylene group, B is selected from the group consisting of hydrogen, phenyl and naphthyl, $R_2$ is selected from the group consiting of halogen, nitro, $C_1$-$C_6$ alkyl and $C_1$-$C_6$ alkoxy, m is 0 or an integer of from 1 to 3, n is 0 or 1, and p is 0 or an integer of from 1 to 3 but when B is hydrogen both n and p are 0.

The alkylene group "Z" may be straight chain or branched so as to yield, for example, 2-ethanone-, 2-propanone- or 3-propanone oxime derivatives and is preferably methylene as is the alkylene group X. Alkyl or alkoxy groups $R^1$, $R^2$, optionally present as substituents in A or B, preferably contain from 1 to 4 carbon atoms. Particularly preferred such alkyl or alkoxy groups are methyl and methoxy. A and B preferably denote phenyl. When the compounds are present in salt form, it is preferably the nitrate form.

A particularly preferred class of compounds according to the present invention are those of general formula I':

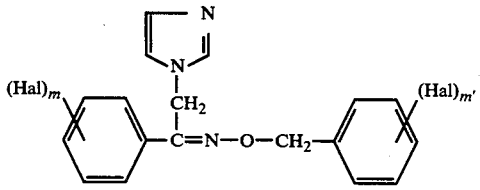

wherein Hal denotes a halogen atom and m and m' which are the same or different denote 0, 1, 2 or 3. Particularly preferred compounds of this type are those wherein at least one of m and m' is 1, 2 or 3.

The imidazolyl oxime ethers according to the present invention have been found to show interesting effects on lower plant organisms and in this connection display, in particular, anti-mycotic and bactericidal effects, which may be employed for chemotherepeutic purposes in human and veterinary medicine, as well as in plant protection. Compounds which have been found to be of particular value in this connection are the following:

1-(2,4-Dichlorophenyl)-2-(1H-imidazol-1-yl)-O-(2,4-dichlorobenzyl)-ethanone-oxime 1-(4-Bromophenyl)-2-(1H-imidazol-1-yl)-O-(2,4-dichlorobenzyl)-ethanone-oxime 1-Phenyl-2-(1H-imidazol-1-yl)-O-(3,4-dichlorobenzyl)-ethanone-oxime 1-(4-Chlorophenyl)-2-(1H-imidazol-1-yl)-O-(2-chlorobenzyl)-ethanone-oxime, and 1-(4-Chlorophenyl)-2-(1H-imidazol-1-yl)-O-(4-bromobenzyl)-ethanone-oxime.

The imidazolyl oxime ethers of this invention may be produced by a process which comprises reacting a compound of the general formula

wherein alk and A have the meaning set out above, with a compound of general formula $$Y - B \qquad (III)$$

wherein B has the meaning given above, X and Y being two groups, which, when said compounds of general formulae II and II are brought together, react together to yield the grouping =N—O—.

In carrying out this preparative procedure, it is possible to react a compound II wherein X denotes an oxygen atom with a compound of formula III wherein Y denotes the grouping $H_2$=N—O—, as in, for example, the compound O-benzyl hydroxylamine.

However, the starting material of general formula II which is preferably employed is a metal oximate, in which case, therefore, X denotes the grouping =N—OM wherein M denotes a metal atom, in particular an alkali or alkaline earth metal or a heavy metal, for example silver. In this case, a reaction partner of formula III is used in which Y is a halogen atom; reaction partners III in such a case are exemplified by benzylchloride and benzylbromide.

The aforesaid metal oximates can be produced, for example, by reaction of the corresponding oximes (compounds of formula II having the grouping =N—OH instead of X) with sodium hydride. The oxime compounds are obtainable by reaction of 2-imidazolyl-ethanones carrying a substituent in the 1-position with hydroxylamine. The 1-substituted-2-imidazolyl ethanones for their part can be produced by condensation of 1-substituted-2-haloethanones with imidazole.

The oximes mentioned above, these being compounds of general formula II with =N—OH instead of X are described in J. Med. Chem. 12, 784 (1969). In contrast, the oxime ethers of the present invention have not hitherto been disclosed.

The oxime ethers of the present invention are preferably isolated in the form of their acid addition salts with inorganic or organic acids, for example hydrochloric acid, nitric acid or tartaric acid, in which form they may be administered for therapeutic purposes.

For therapeutic use, the compounds of this invention can be made up in accordance with well known pharmaceutical techniques, into compositions having as an essential active ingredient, a compound of the invention in association with a non-toxic pharmaceutical carrier therefor, e.g. a solvent or a pharmaceutical base for topical or vaginal application (ointment, cream, spray, gel, lotion etc.). If desired, the compositions can be made up in a dosage unit form suitable for the particular mode of administration, the quantity of active ingredient in each dosage unit being such that one or more units are required for each therapeutic administration. This dosage unit may exist, for example, in the form of a tablet, pill, sachet, suppository, packaged powder or encapsulated powder for oral administration or in the form of a sterile injectable solution or suspension, if desired contained in an ampoule, for parenteral administration.

The following examples illustrate the invention:

EXAMPLE 1

1-(2,4-Dichlorophenyl)-2-(1H-imidazol-1-yl)-O-(2,4-dichlorobenzyl)-ethanone oxime nitrate

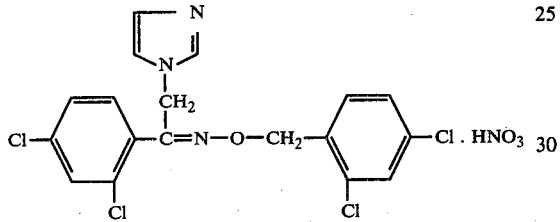

a. Preparation of the starting product: 1-(2,4-dichlorophenyl-2-(1H-imidazol-1-yl)-ethanonoxime 35.6 g of 2,4-dichlorophenacylimidazole are dissolved in a mixture of 260 ml ethanol and 26 ml pyridine. The solution is mixed with 14.9 g of hydroxylammonium chloride and heated for 3 hours under reflux. Subsequently, the reaction mixture is concentrated in a rotation evaporator under reduced pressure, the residue is taken up in water and some ammonium hydroxide solution is added thereto. The heavy precipitate formed is separated off by filtration and is washed free from the filtrate with water. As a result of recrystallisation from ethanol, there is obtained a colourless crystallised substance of melting point 218° to 220° C. in a yield of 70%.

$C_{11}H_9Cl_2N_3O$ (270.1): Calc.: C, 48.91; H, 3.36; N, 15.56; Cl, 26.25. Obtained: C, 48.83; H, 3.26; N, 15.59; Cl, 26.24.

b. Production of the oxime ethers according to the invention 13.5 g of the oxime whose production is described under (a) are dissolved in 100 ml dimethylformamide ("DMF") and 1.2 g of sodium hydride are mixed in, whereupon an exothermic reaction is allowed to take place on its own with stirring. After cessation of evolution of hydrogen, a solution of 9.8 g of 2,4-dichlorobenzylchloride in 10 cc DMF is added dropwise with continuous stirring and the stirring is carried on for 2 further hours. The reaction is then taken to completion at a bath temperature of 80° C., after which the reaction mixture is evaporated in a rotation evaporator under reduced pressure and the residue is dissolved in 100 ml ethanol. After filtering off of undissolved matter, the solution is stirred with 400 ml 2N nitric acid for the conversion of free base to the nitrate.

The liquid standing over the heavy deposits which have separated out is separated off by decanting, whereupon an isomer is obtained which after recrystallisation from ethanol is obtained in a yield of 5.2 g and having a melting point 137° to 138° C.

$C_{18}H_{13}Cl_4N_3O$ (492.2): Calc.: C, 43.93; H, 2.87; N, 11.38; Cl, 28.82. Obtained: C, 43.82; H, 2.79; N, 10.99; Cl, 28.90.

The other isomer of melting point 163° to 164° C. is obtained if the reaction described under (a) is carried out in the absence of pyridine and the oxime then is used as starting material for reaction (b).

EXAMPLE 2

1-(2-Naphthyl)-2-(1H-imidazol-1-yl)-O-(2,4-dichlorobenzyl)-ethanone oxime

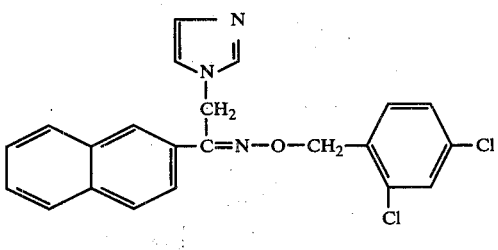

a. Preparation of the starting product: 1-(2-Naphthyl)-2-(1H-imidazol-1-yl)-ethanone oxime To a solution of 12.5 g of 2-bromoacetylnaphthalene in 10 ml acetonitrile are added 8.5 g imidazole, whereupon an exothermic reaction takes place. After being allowed to stand for 2 hours, the reaction mixture is evaporated in a rotation evaporator under reduced pressure. The residue is treated several times with water and is then dissolved in ethanol, purified with active carbon, filtered and strongly concentrated. The 1-(2-Naphthyl)-2-(1H-imidazol-1-yl)-ethanone obtained is isolated in crystalline form as the nitrate by addition of $2N.HNO_3$, which nitrate after recrystallisation from water melts at 186° C. with decomposition. The oxime of melting point 201° to 202° C. (recrystallisation from water) is obtainable from the thus formed ketone in the manner described under (a) in Example 1.

b. Production of the oxime ether according to the invention

A solution of 10.5 g of the 1-(2-naphthyl)-2-(1H-imidazol-1-yl)-ethanone oxime produced according to the foregoing paragraph a) in 20 ml DMF is added dropwise and with stirring to a suspension of 1.0 g NaH in 10 ml DMF. After the termination of the addition, the stirring is continued for 2 hours, whereupon a solution of 8.2 g of 2,4-dichlorobenzyl chloride is added thereto again dropwise and with stirring and is continuously further stirred initially without warming for 4 hours and subsequently for a short time at 50° to 60° C. Then the solvent is distilled off under reduced pressure and the residue is treated with water. The crude product seperated off by filtration is dissolved in alcohol to which some water and active carbon and added. After filtration, further water is added to the hot solution so that no turbidity is allowed to appear and the product is then allowed to crystallise out from the solution when cold. Melting point 126° to 127° C.

$C_{22}H_{17}Cl_2N_3O$ (410.3): Calc.: C, 64.40; H, 4.18; N, 10.24; Cl, 17.28. Found: C, 64.88; H, 4.00; N, 9.72; Cl, 17.33.

EXAMPLE 3

1-(2,4-Dichlorophenyl)-2-(1H-imidazol-1-yl)-O-benzyl-ethanone oxime nitrate 5.1 g (0.02 mol) of 2,4-dichlorophenacyl imidazole are dissolved together with 3.2 g (0.02 mol) of O-benzylhydroxylaminehydrochloride in 50 ml of ethanol and the solution is heated for 3 hours under reflux. Next; complete evaporation is effected in a rotation evaporator. The residue is first treated with dilute ammonium hydroxide. After the decanting off of the washing liquids, the remaining residue is dissolved in alcohol and converted with 20 ml $2N.HNO_3$ to the nitrate which undergoes crystallisation. This is separated off by filtration, washed completely with water and crystallised out from isopropanol. In this way, colourless crystals of melting point 119° to 122° C. are obtained. Yield 4.5 g.

$C_{18}H_{15}Cl_2N_3O \cdot HNO_3$ (423.3): Calc.: C, 51.08; H, 3.81; N, 13.24; Cl, 16.75. Found: C, 51.13; H, 3.81; N, 13.09; Cl, 16.86.

EXAMPLE 4

Further examples of substituted 2-(1H-imidazol-1-yl)-ethanone oximes produced by analogous procedures to those described in Examples 1 to 3 are:

(i) the 1-phenyl-O-(2,4-dichlorobenzyl) derivative
mp. 83°–84° C. (free base)
mp. 157° C. (nitrate)
(ii) the 1-(2,4-dichlorophenyl)-O-(4-chlorobenzyl)-derivative
mp. 121°–126° C. (nitrate)
(iii) 1-(4-chlorophenyl)-O-(2,4-dichlorobenzyl) derivative
mp. 142°–147° C. (nitrate)
(iv) the 1-(2,4-dimethylphenyl)-O-(2,4-dichlorobenzyl)-derivative
mp. 151°–154° C. (nitrate)
(v) the 1-(4-bromophenyl)-O-(2,4-dichlorobenzyl)-derivative
mp. 152°–154° C. (nitrate)
(vi) the 1-(4-fluorophenyl)-O-(2,4-dichlorobenzyl)-derivative
mp. 124°–126° C. (nitrate)
(vii) the 1-phenyl-O-benzyl derivative
mp. 153° C. (nitrate)
(viii) the 1-phenyl-O-(4-chlorobenzyl)derivative
mp. 153°–154° C. (nitrate)
(ix) the 1-(2,4-dichlorophenyl)-O-benzyl derivative
mp. 119°–122° C. (nitrate)
(x) the 1-phenyl-O-(3,4-dichlorobenzyl)derivative
mp. 144° C. (nitrate)
(xi) the 1-phenyl-O-(1-methyl-naphthyl)derivative
mp. 165°–166° C. (nitrate)
(xii) the 1-(4-chlorophenyl)-O-(3,4-dichlorobenzyl)-derivative
mp. 152°–155° C. (nitrate)
(xiii) the 1-phenyl-O-(2,6-dichlorobenzyl)derivative
mp. 138°–140° C. (nitrate)
(xiv) the 1-(4-chlorophenyl)-O-(1-methyl-naphthyl)-derivative
mp. 163°–165° C. (nitrate)
(xv) the 1-(4-chlorophenyl)-O-(2-chlorobenzyl)derivative
mp. 116°–118° C. (nitrate)
(xvi) the 1-(4-chlorophenyl)-O-(2-methylbenzyl)derivative
mp. 167°–169° C. (nitrate)
(xvii) the 1-(4-chlorophenyl)-O-(2,6-dichlorobenzyl)-derivative
mp. 180° C. (nitrate)
(xviii) the 1-(4-chlorophenyl)-O-(4-fluorobenzyl)derivative
mp. 170° C. (nitrate)
(xix) the 1-(4-chlorophenyl)-O-(4-bromobenzyl)derivative
mp. 146° C. (nitrate)
(xx) the 1-phenyl-O-(4-bromobenzyl)derivative
mp. 151°–152° C. (nitrate)
(xxi) the 1-(4-bromophenyl)-O-(4-bromobenzyl)derivative
mp. 167° C. (nitrate)
(xxii) the 1-(2,4-dichlorophenyl)-O-(4-bromobenzyl)-derivative
mp. 162°–163° C. (nitrate)
(xxiii) the 1-(4-bromophenyl)-O-(4-chlorobenzyl)-derivative
mp. 169°–170° C. (nitrate)
(xxiv) the 1-(4-iodophenyl)-O-(2,4-dichlorobenzyl)-derivative
mp. 163°–164° C. (nitrate)
(xxv) the 1-(4-chlorophenyl)-O-(4-chlorobenzyl)derivative
mp. 157°–158° C. (nitrate)
(xxvi) the 1-(4-chlorophenyl)-O-phenethyl derivative
mp. 147°–148° C. (nitrate)
(xxvii) the 1-(4-chlorophenyl)-O-(1-phenoxy-ethan-2-yl)derivative
mp. 121°–123° C. (nitrate)
(xxviii) the 1-(4-chlorophenyl)-O-ethyl derivative
mp. 117°–119° C.

Employing the same methods, the following further compounds were produced by the process of this invention:

(xxix) 1-phenyl-2-(1H-imidazol-1-yl)-O-(2,4-dichlorobenzyl)-propanone oxime nitrate (mp. 151°–152° C.) of the formula:

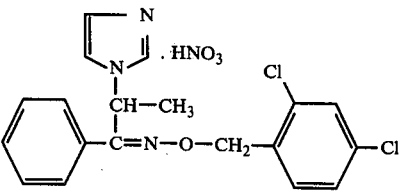

(xxx) 1-phenyl-3-(1H-imidazol-1-yl)-O-(2,4-dichlorobenzyl)propanone oxime nitrate (mp. 110°–110° C.) of the formula:

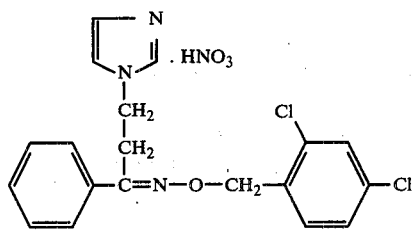

We claim:
1. A compound of the formula (I)

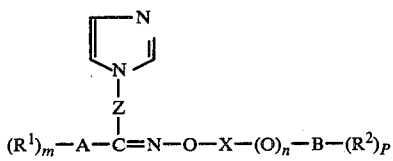

in the form of either of its two possible geometric isomers or a mixture thereof in free base form or therapeutically effective salt form as a result of reaction with an acid, in which formula:
Z is selected from the group consisting of straight and branched chain $C_1$–$C_4$ alkylene groups,
A is selected from the group consisting of phenyl and naphthyl,
$R^1$ is selected from the group consisting of halogen, nitro, $C_1$–$C_6$ alkyl and $C_1$–$C_6$ alkoxy,
X is $C_1$–$C_8$ alkylene group,
B is selected from the group consisting of hydrogen, phenyl and naphthyl,
$R^2$ is selected from the group consisting of halogen, nitro, $C_1$–$C_6$ alkyl and $C_1$–$C_6$ alkoxy,
$m$ is 0 or an integer of from 1 to 3,
$n$ is 0 or 1, and
$p$ is 0 or an integer of from 1 to 3 but when B is hydrogen both $n$ and $p$ are 0.

2. The compound of claim 1 wherein both Z and X in said formula (I) are methylene groups.

3. The compound of claim 1 wherein in said formula (I) both A and B are phenyl.

4. The compound of claim 1 wherein said therapeutically effective salt form is the nitrate form.

5. The compound of claim 1 which is 1-(2-naphthyl)-2-(1H-imidazol-1-yl)-O-(2,4-dichlorobenzyl)-ethanone oxime or a therapeutically effective acid addition salt thereof.

6. The compound of claim 1 which is 1-phenyl-2-(1H-imidazol-1-yl)-O-(2,4-dichlorobenzyl)-propanone oxime or a therapeutically effective acid addition salt thereof.

7. A compound of the formula (I')

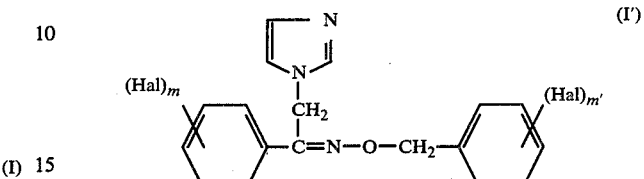

wherein Hal is a halogen atom and $m$ and $m'$ are independently 0 or an integer of from 1 to 3, said compound being in the form of either of its two possible geometric isomers or a mixture thereof in free base form or therapeutically effective salt form as a result of reaction with an acid.

8. The compound of claim 7 wherein at least one of $m$ and $m'$ is an integer of from 1 to 3.

9. The compound of claim 7, wherein said therapeutically effective salt form is the nitrate form.

10. The compound of claim 7 which is 1-(2,4-dichlorophenyl)-2-(1H-imidazol-1-yl)-O-(2,4-dichlorobenzyl)-ethanone oxime or a therapeutically effective acid addition salt thereof.

11. The compound of claim 7 which is 1-(4-bromophenyl)-2-(1H-imidazol-1-yl)-O-(2,4-dichlorobenzyl)-ethanone oxime or a therapeutically effective acid addition salt thereof.

12. The compound of claim 7 which is 1-phenyl-2-(1H-imidazol-1-yl)-O-(3,4-dichlorobenzyl)-ethanone oxime or a therapeutically effective acid addition salt thereof.

13. The compound of claim 7 which is 1-(4-chlorophenyl)-2-(1H-imidazol-1-yl)-O-(2-chlorobenzyl)-ethanone oxime or a therapeutically effective acid addition salt thereof.

14. The compound of claim 7 which is 1-(4-chlorophenyl)-2-(1H-imidazol-1-yl)-O-(4-bromobenzyl)-ethanone oxime or a therapeutically effective acid addition salt thereof.

* * * * *